United States Patent
Kim et al.

(10) Patent No.: US 8,604,271 B2
(45) Date of Patent: Dec. 10, 2013

(54) HUMANIZED NSG MOUSE, METHOD OF PRODUCING THE SAME AND USE THEREOF

(75) Inventors: Sung Joo Kim, Seoul (KR); Yun Shin Chung, Seoul (KR); Sung Yeon Joo, Seoul (KR); Bong Kim Choi, Masan-si (KR); Jae Won Joh, Gyeonggi (KR)

(73) Assignee: Samsung Life Welfare Foundation (KR)

( * ) Notice: Subject to any disclaimer, the term of this patent is extended or adjusted under 35 U.S.C. 154(b) by 0 days.

(21) Appl. No.: 13/227,233

(22) Filed: Sep. 7, 2011

(65) Prior Publication Data

US 2012/0066780 A1    Mar. 15, 2012

Related U.S. Application Data

(63) Continuation of application No. PCT/KR2010/002638, filed on Apr. 27, 2010.

(30) Foreign Application Priority Data

Apr. 27, 2009 (KR) .................. 10-2009-0036730

(51) Int. Cl.
*A01K 67/027* (2006.01)
*A61K 35/26* (2006.01)
*A61K 35/28* (2006.01)
*A61K 35/32* (2006.01)

(52) U.S. Cl.
USPC .............. 800/8; 424/93.7; 424/549; 424/577; 424/580

(58) Field of Classification Search
USPC .................. 800/8; 424/93.7, 577, 580, 549
See application file for complete search history.

(56) References Cited

U.S. PATENT DOCUMENTS

| | | | |
|---|---|---|---|
| 5,057,598 A | * | 10/1991 | Pollack et al. ............. 424/150.1 |
| 7,145,055 B2 | | 12/2006 | Ito et al. |
| 2007/0011753 A1 | * | 1/2007 | Ito et al. ......................... 800/6 |

FOREIGN PATENT DOCUMENTS

WO    2006049439 A1    5/2006

OTHER PUBLICATIONS

Lapidot et al. (1997) J. Mol. Med., vol. 75, 664-673.*
Shultz et al. (2005) J. Immunol., vol. 174, 6477-6489.*
McDermott, et al.; "Comparison of Human Cord Blood Engraftment Between Immunocompromised Mouse Strains"; Blood. vol. 116 (2) pp. 193-200 (Jul. 15, 2010).
Bente, et al.; "Dengue Fever in Humanized NOD/SCID Mice"; Journal of Virology 2005; vol. 79: pp. 13797-13799.
Varga, et al.; "Detection of human Hematopoietic Stem Cell Engraftment in the Livers of Adult Immunodeficient Mice by an Optimized Flow Cytometric Method"; Stem Cell Studies vol. 1 (1); Nov. 24. 2010; 26 pages.
Shultz et al.; "Human Lymphoid and Myeloid Cell Development in NOD/LtSz-scid IL2Rynull Mice Engrafted with Mobilized Human Hemopoietic Stem Cells 1,2"; The Journal of Immunolology 2005; 174: pp. 6477-6489.
International Search Report and Written Opinion of the International Searching Authority; Application No. PCT/KR2010/002638; Issued: Jan. 19, 2011; 6 pages.
Ito, et al; "NOD/SCID/y Mouse: An Excellent Recipient Mouse Model for Engraftment of Human Cells"; Blood. 2002; 100: pp. 3175-3182.
Carsetti, et al.; "Peripheral Development of B Cells in Mouse and Man"; Immunological Reviews; vol. 197; pp. 179-191; 2004.
Greiner, et al.; "SCID Mouse Models of Human Stem Cell Engraftment" Stem Cells 1998; 16: pp. 166-177.

* cited by examiner

*Primary Examiner* — Anne Marie S Wehbe
(74) *Attorney, Agent, or Firm* — St. Onge Steward Johnston & Reens LLC (57) ABSTRACT

A mouse model in which human fetal thymus and human fetal bone fragments are transplanted into NSG mice, a method of producing the same, and a use thereof.

5 Claims, 6 Drawing Sheets

HUMANIZED NSG MOUSE, METHOD OF PRODUCING THE SAME AND USE THEREOF

CROSS-REFERENCE TO RELATED APPLICATIONS

The present application is a continuation of pending International patent application PCT/KR2010/002638 filed on Apr. 27, 2010 which designates the United States and claims priority from Korean Patent Application No. 10-2009-0036730 filed on Apr. 27, 2009, the content of which is incorporated herein by reference.

FIELD OF THE INVENTION

The present invention relates to a mouse model which human fetal thymus and fetal bone fragments are transplanted into NSG mice, a method of producing the same, and a use thereof.

BACKGROUND OF THE INVENTION

Because technical and ethical issues impose limitations on pathological studies of human subjects, disease models using animals known to be genetically very similar to human beings are valuable alternatives. Model animals are afflicted with a target disease, and various therapeutic agents are applied to search for treatment methods. However, because it is uncertain whether the same effects may be obtained in humans with use of therapeutic agents known to have therapeutic effects in animal disease models, and direct application of therapeutic agents identified in animal disease models for humans is prohibited, such therapeutic agents must undergo many procedures until they are approved for clinical application in humans.

Recently, efforts have been actively made to generate humanized animal models with a human-like immune system in order to establish animal disease models more effectively than ever. Among humanized animal models, in particular, methods of transplanting hematopoietic stem cells into immunodeficient mice have been established humanized mice. As a result of transplantation of human CD34+ cells into severe combined immune-deficient (SCID) mice, small numbers of human hematopoietic stem cell-derived cells were detected in all tissues and the cells were reconstituted in the tissues of the mice (Greiner D L, Hesselton R A and Shultz L D, Stem Cells 1998; 16: 166-77). When human CD34+ hematopoietic stem cells were transplanted into non-obese diabetic/SCID (NOD/SCID) mice with impaired NK cell function, human cells were greatly reconstituted in tissues than those of SCID mice. However, human cells were detected mainly in bone marrow, and human T cells were not still developed in the initial period after transplantation (Bente D A, Melkus M W, Gracia J V and Rico-Hesse R, J Virol 2005; 79:13797-9).

Although NOD/SCID mice lack T and B cells, the mice still have NK cell functions and take disadvantage of their short life spans due to spontaneous formation of lymphoma. In order to improve these limitations, NSG mice with impaired NK cell functions as well as defective T and B cells (NOD/SCID/IL2 receptor γ null) were developed (Shultz L D, et al., J. Immunol. 2005; 174: 6477-6489). Because NSG mice have life spans that are twice longer than those of NOD/SCID mice, they are appropriate for long-term monitoring after transplantation of human cells. It was confirmed that human B, T, and NK cells might be reconstituted by a single transplantation of hematopoietic stem cells without simultaneous transplantation of human hematopoietic tissues such as human fetal thymus or human fetal liver into NSG mice (Blood. 2002; 100: 3175-3182). When only hematopoietic stem cells were transplanted into NSG mice, 30 to 90% of human cells were detected due to successful engraftment and differentiation of the human cells. However, most of the B and T cells were not differentiated in normal ratios, and B cells were predominantly distributed unlike the distribution of immune cells in normal human peripheral blood.

Therefore, there still exists a need for a humanized mouse with a ratio of mature human B and T cells that is more similar to those in the human than those in previously established humanized mice.

SUMMARY OF THE INVENTION

The present invention provides a humanized mouse useful in transplantation of human cells.

The present invention also provides a method of producing the humanized mouse.

The present invention also provides a method of producing human antibodies by using the humanized mouse.

The present invention also provides a method of analyzing self-renewal and differentiation of human stem cells by using the humanized mouse.

According to an aspect of the present invention, there is provided an NSG mouse which human fetal thymus and human fetal bone fragment are transplanted.

The NSG mouse refers to a non-obese diabetic (NOD) mouse which is double homozygous for the severe combined immune-deficient (SCID) mutation and the interleukin 2Rγallelic mutation (γnull). The SCID mutation refers to a mutation which results in deficiencies of functional B and T cells. For example, SCID mice (C.B.-17-Prkdc$^{scid}$) have defects in rearrangement of B cell receptor (BCR) and T cell receptor (TCR), resulting in deficiencies of functional B and T cells. The NOD scid gamma (NSG) mice are also known as NOD/SCIDγnull mice or NOD/SCID IL-2RγKO mice. NSG mice were developed in the laboratory of Dr. Leonard Shultz at The Jackson Laboratory (USA). The NSG mice may be commercially available from The Jackson Laboratory or prepared by known methods (Shultz L D, et al., J. Immunol. 2005; 169: 204-209). For example, NSG mice may be generated by backcross matings of C57BL/6J-γnull mice with NOD/SCID mice nine times. It is known that NSG mice lack functional T and B cells and have reduced macrophage function, absent NK cell or NK activity, and reduced dendritic cell function. It is known that NSG mice have higher level of xenograft engraftment than those in NOD/SCID mice or $\beta_2$-microglobulin-deficient NOD/LtSz-SCID (NOD/SCID/$\beta_2$m null).

Human fetal thymus and human fetal bone fragment are transplanted into the NSG mice, which have enhanced engraftment levels of xenograft, compared to those in NOD/SCID mice.

In the mice, the human fetal thymus may be transplanted under a renal capsule, and the fetal human bone fragments may be transplanted subcutaneously.

The mice may be ones in which human stem cells are further transplanted. The human stem cells may be, for example, hematopoietic stem cells. The hematopoietic stem cells may be selected from the group consisting of adult bone marrow, umbilical cord blood, fetal liver, and mobilized peripheral blood. For example, the hematopoietic stem cells may be human fetal liver- or umbilical cord blood-derived CD34+ cells. The human stem cells may be transplanted by intravenous administration.

The mice may have a more humanized immune system than that in NOD/SCID mice or NOD/SCID/$\beta_2$m null mice. For example, the mice may have mature human T or B cells, for example, in lymph nodes, spleen, and/or bone marrow with a ratio that is more similar to those in the human than those in NOD/SCID mice or NOD/SCID/$\beta_2$m null mice. The mature human B cells may be CD19+ IgM-IgD+ cells. The mature human T cells may be CD4+ or CD8+ cells.

In the mice, each of the human fetal thymus and human fetal bone fragment may be derived from the same individual. The human stem cells may be derived from the same individual or a different individual from which the human fetal thymus and human fetal bone fragment are derived.

According to another aspect of the present invention, there is provided a method of producing antibodies binding to an antigen, including: immunizing the antigen to an NSG mouse which human fetal thymus, human fetal bone fragment, and human stem cells are transplanted; and isolating the antibodies from serum of the immunized mouse.

The method includes immunizing an antigen to the NSG mouse which human fetal thymus, human fetal bone fragment, and human stem cells are transplanted.

The NSG mouse which human fetal thymus, human fetal bone fragment, and human stem cells are transplanted is the same as described above. Immunization is known to those skilled in the art, and known immunization methods may be used. It is appreciated by those skilled in the art that according to a selected antigen, a high immune response may be induced in a mouse to be administered by selecting an appropriate dosage regimen and immunizing the antigen to the mouse. The antigen includes, but is not specifically limited to, any material which may induce an immune response in the mouse. The antigen may be, for example, protein, sugar, or lipid.

The method includes isolating antibodies from serum of the immunized mouse. The step may be performed by known methods of isolating antibodies. For example, blood may be drawn from the immunized mouse and subjected to centrifugation to obtain serum. Antibodies may be isolated from the serum.

According to another aspect of the present invention, there is provided a method of producing antibodies binding to an antigen, including: immunizing the antigen to the NSG mouse which human fetal thymus, human fetal bone fragment, and human stem cells are transplanted; and isolating B cells which produce the antibodies binding to the antigen from the immunized NSG mouse.

The method includes immunizing the antigen to an NSG mouse into which human fetal thymus, human fetal bone fragment, and human stem cells are transplanted, and the step is the same as described above.

The method includes isolating B cells which produce the antibodies binding to the antigen from the immunized NSG mouse. The isolating the B cells may include not only isolating B cells, but also increasing the frequency of B cells. The B cells may be isolated as lymphoid cells or splenocytes including the B cells. The isolated B cells may be incubated and used to produce antibodies.

The method may further include immortalizing the isolated B cells. Methods of immortalizing B cells are known in the art. The immortalizing may include, for example, fusing the isolated B cells with a myeloma cell line. The method may further include selecting cells which produce antibodies specifically binding to the antigen among the immortalized cells. The selected cells which produce antibodies specifically binding to the antigen may be incubated and used to produce and isolate the antibodies.

According to another aspect of the present invention, there is provided a method of producing a humanized mouse, including: transplanting human fetal thymus and human fetal bone fragment into an NSG mouse.

The human fetal thymus may be transplanted under a renal capsule, and the human fetal bone fragment may be transplanted subcutaneously.

The method may further include transplanting human stem cells. The transplanting of the human stem cells may be performed by intravenous administration. The human stem cells may be hematopoietic stem cells. The hematopoietic stem cell may be selected from the group consisting of adult bone marrow, umbilical cord blood, fetal liver, and mobilized peripheral blood.

According to another aspect of the present invention, there is provided a method of analyzing cells self renewed and differentiated from human stem cells, including: transplanting the human stem cells into an NSG mouse which human fetal thymus and human fetal bone fragment are transplanted; and analyzing the cells self renewed and differentiated from the human stem cells.

The method includes transplanting human stem cells into an NSG mouse which human fetal thymus and human fetal bone fragment are transplanted. The transplanting of the human stem cells may be performed, for example, by caudal vein administration. The human stem cells may be hematopoietic stem cells. The hematopoietic stem cell may be ones which are selected from the group consisting of adult bone marrow, umbilical cord blood, fetal liver, and mobilized peripheral blood-derived hematopoietic stem cell.

The method includes analyzing cells self renewed and differentiated from the human stem cells. The analyzing of the cells may be performed by known methods. The self renewed and differentiated cells may be harvested from the mouse and analyzed at the cellular or tissue level. For example, the cells may be analyzed by performing binding of human cells to human-specific antibodies to obtain a complex. The analysis may be performed by specifically staining certain cells, and then by visualization or image analysis of the cells. For example, the analysis may be performed by flow cytometry. The analysis includes identification of a type, the frequency and differentiation level of certain cell.

An NSG mouse which human fetal thymus and human fetal bone fragment are transplanted according to an aspect of the present invention may be used to produce a mouse with human immune cell, compared to an NSG mouse without transplantation.

Human antibodies may be highly efficiently produced by a method of producing an antigen-specific antibody according to another aspect of the present invention, compared to an NSG mouse without transplantation.

The proliferation and differentiation of human stem cells may be efficiently observed by a method of analyzing cells self renewed and differentiated from human stem cells according to another aspect of the present invention, compared to an NSG mouse without transplantation.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to embodiments. However, the embodiments are provided for illustrative purposes only, and the scope of the present invention is not limited thereto in any manner.

EXAMPLE 1

Preparation of NSG mice which human fetal thymus, human fetal bone fragment, and human fetal liver or umbilical cord blood-derived hematopoietic stem cells are transplanted.

Human fetal liver or umbilical cord blood-derived hematopoietic stem cells were transplanted into the mice, which were transplanted previously human fetal thymus and human fetal bone fragment.

(1) Transplantation of Human Fetal Thymus, Human Fetal Bone Fragment, and Human Fetal Liver or Umbilical Cord Blood-Derived Hematopoietic Stem Cells into NSG Mice On the day of transplantation, cryopreserved human fetal thymus (1 mm$^3$) and human fetal bone fragment (3 mm$^3$) tissues (Advanced Bioscience Resource, INC., USA) or human fetal thymus (1 mm$^3$) and human fetal bone fragment (3 mm$^3$) were prepared by dissecting dead-born fetus, an IRB (Institutional Review Board)-approved (Samsung Medical Center). 8 week-old NSG mice (Jackson Laboratory, USA) were anesthetized, one piece of the human fetal thymus prepared by dissection was transplanted under the left renal capsule of the anesthetized mouse at a time, and incised membranes were sutured using a hemostat. One piece of the human fetal bone fragments prepared by dissection was also transplanted subcutaneously into a region between the left upper limb and axilla of the anesthetized mouse at a time, and the membranes were sutured to prepare an experimental group.

In addition, a control group was prepared without transplantation of human fetal thymus and human fetal bone fragment into NSG mice by performing the same surgery and hematopoietic stem cell transplantation procedure as in the experimental group.

(2) Transplantation of Hematopoietic Stem Cells

All the mice in the experimental and control group transplanted with human fetal tissues in (1) were recovered for 3 weeks after the surgery. Preconditioning was achieved by intraperitoneally administering busulfan (20 mg/kg) to mice in the experimental group and control group at 3 weeks after the surgery, and then human fetal liver or umbilical cord blood-derived hematopoietic stem cells were transplanted into the mice within 24 hours. Human fetal liver or human umbilical cord blood-derived hematopoietic stem cells were labeled with a biotinylated anti-CD34 antibody, MACS equipment (Miltenyi Biotech, Germany) was used for sorting, and 99% or more of CD34+ cells were isolated.

A 31-gauge insulin syringe (BD Bioscience) was used to inject CD34+ hematopoietic stem cells through the tail veins of the mice at $1\times10^5$ cells/0.1 ml/mouse.

(3) Identification of Engraftment and Differentiation of Human Cells by Flow Cytometry.

Blood was drawn from the tail of each mouse at 8 weeks after transplantation of hematopoietic stem cells into the NSG mice in the experimental and control group generated as in (2), and human immune cells in peripheral blood in the mice were observed by flow cytometry at a four-week interval. For observation of the immune cells, 200 µl of blood was drawn from the caudal vein of each mouse, and staining was performed in the following manner to label white blood cells harvested by lysis of red blood cells at room temperature with human CD marker. $10^5$ cells of white blood cells were allowed to react with anti-human CD45-PECy7, anti-human CD19-PE, and anti-human CD3-FITC (eBioscience, Inc., USA) in 1× phosphate buffered saline (PBS) supplemented with 2% fetal bovine serum (FBS) at 4° C. for 30 min under dark conditions and washed once with 1×PBS supplemented with 2% FBS. White blood cells harvested as above were measured using FACS Aria (BD BioScience, USA), a fluorescence activated cell sorter, and the results were analyzed by FACS Diva program (BD Biosciences, USA). As a result, it was found that CD45+ human cells had been engrafted in the mice with high frequency.

Next, the spleen tissues and the bone marrow tissues were isolated from the mice. Spleens of the mice were extracted and passed through a 70 µm mesh strainer (BD Bioscience, USA) to isolate a single cell suspension. In order to isolate bone marrow cells, femurs and tibias were extracted, and each of the upper and lower ends of the femur and tibias were punctured with 18G needle. The bone marrow was flushed with 1×PBS supplemented with 2% FBS by using a 3-ml syringe with a 18G or 21G needle, and the syringe in use was passed 3 or 4 times to prepare a single cell suspension, followed by passing through a 70 µm mesh strainer to remove bone debris from the cells. In order to label white blood cells harvested as above with a differentiated human cell marker, staining was performed in the following manner. $10^5$ cells of white blood cells were allowed to react with anti-human CD45-PECy7 (Phycoerythrin-Cy7), anti-human 19-PE, anti-human IgD-FITC, anti-human CD20-APC, anti-human CD38-PE, anti-human CD19-PECy7, and anti-human IgM-PE and anti-human CD3-fluorescein isothiocyanate (FITC) (eBioscience, Inc., USA) in 1× phosphate buffered saline (PBS) supplemented with 2% fetal bovine serum (FBS) at 4° C. for 30 min under dark conditions and washed once with 1×PBS supplemented with 2% FBS. White blood cell samples harvested as above were measured using FACS Aria (BD BioScience, USA), a fluorescence-activated cell sorter, and the results were analyzed by FACS Diva program (BD Biosciences, USA). The results are shown in FIGS. 1 to 4.

As illustrated in FIGS. 1 to 4, it was confirmed that human hematopoietic stem cells had been engrafted in bone marrow and differentiated in the mice in vivo. In addition, the engrafted hematopoietic stem cells were self-renewed and differentiated into human blood cells including mature B and T cells.

Immunization of NSG mice, which human fetal thymus, human fetal bone fragments, and human fetal liver-derived CD34+ cell had been transplanted, with DNP-KLH mixed with an incomplete adjuvant was performed at 14 weeks after the transplantation. DNP-KLH mixed with a complete adjuvant was intramuscularly administered to the mice at 2 weeks after the immunization. An intrasplenic immunization of the mice with DNP-KLH was performed at 2 weeks after the intramuscular administration. That is, the final immunization was performed at 18 weeks after hematopoietic stem cells had been transplanted into the NSG mice.

Figure 1:
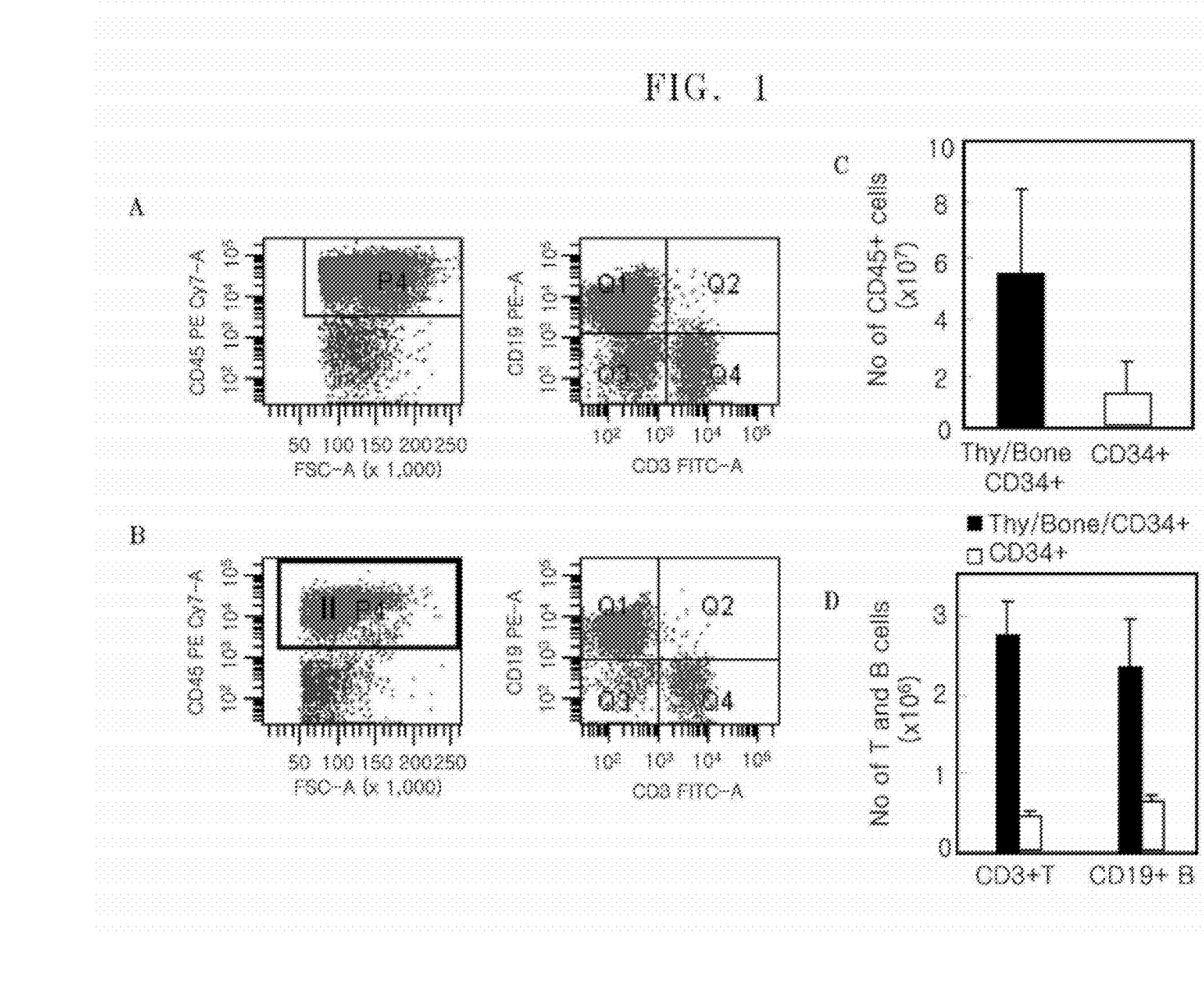
FIG. 1 is a view illustrating the results of splenocytes observed by flow cytometry at 3 to 4 weeks after intrasplenic immunization of NSG mice which human fetal thymus, human fetal bone fragments, and fetal liver or umbilical cord blood-derived CD34+ cells are transplanted; and the mice which only hematopoietic stem cells are transplanted, following immunization of the mice with DNP-KLH by the first and the second intramuscular injections.
Figure 2:
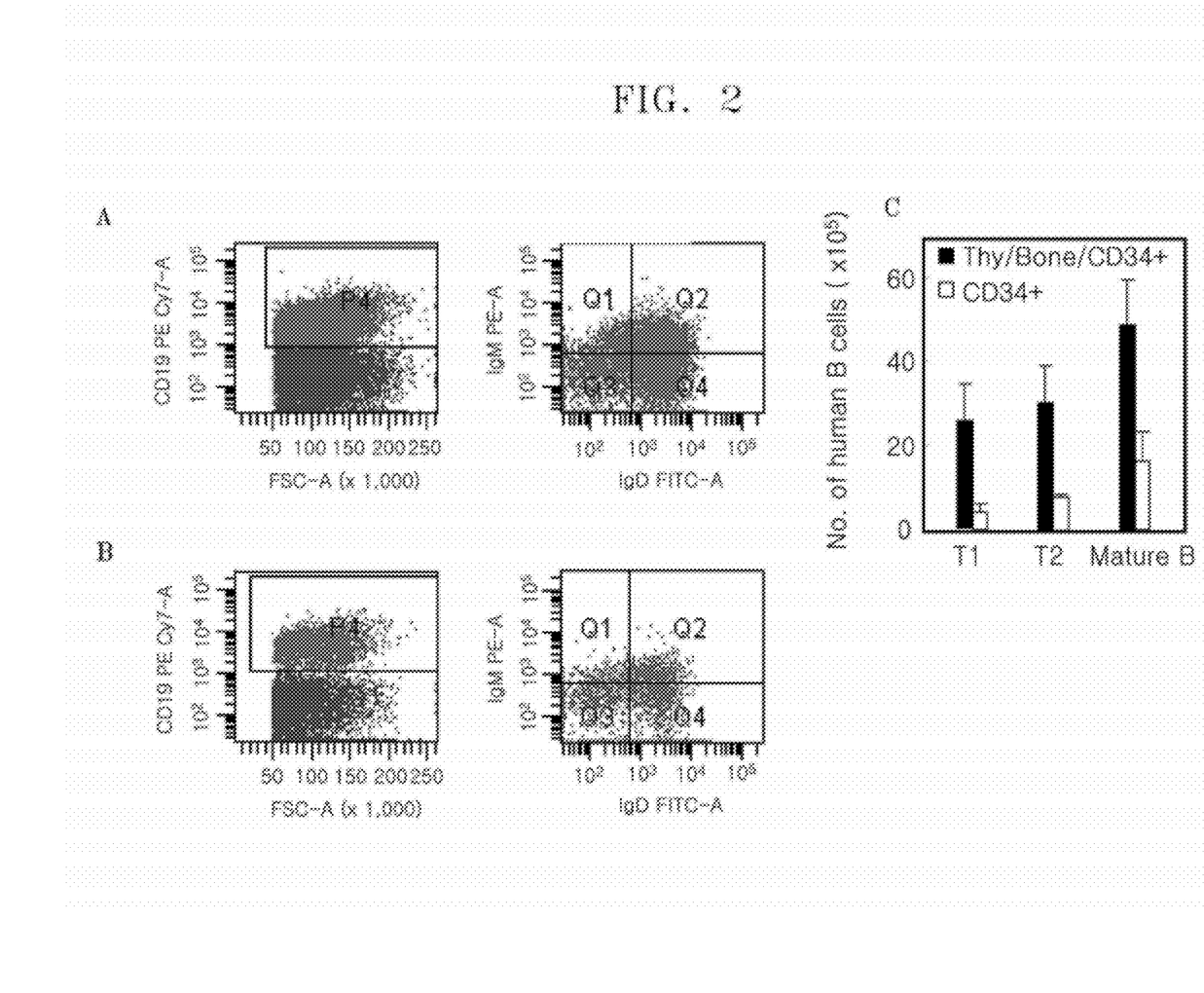
FIG. 2 is a view illustrating results of the splenocytes observed by flow cytometry at 4 weeks after intrasplenic immunization with DNP-KLH of NSG mice which human fetal thymus, human fetal bone fragments, and fetal liver or umbilical cord blood-derived CD34+ cells are transplanted.
Figure 3:
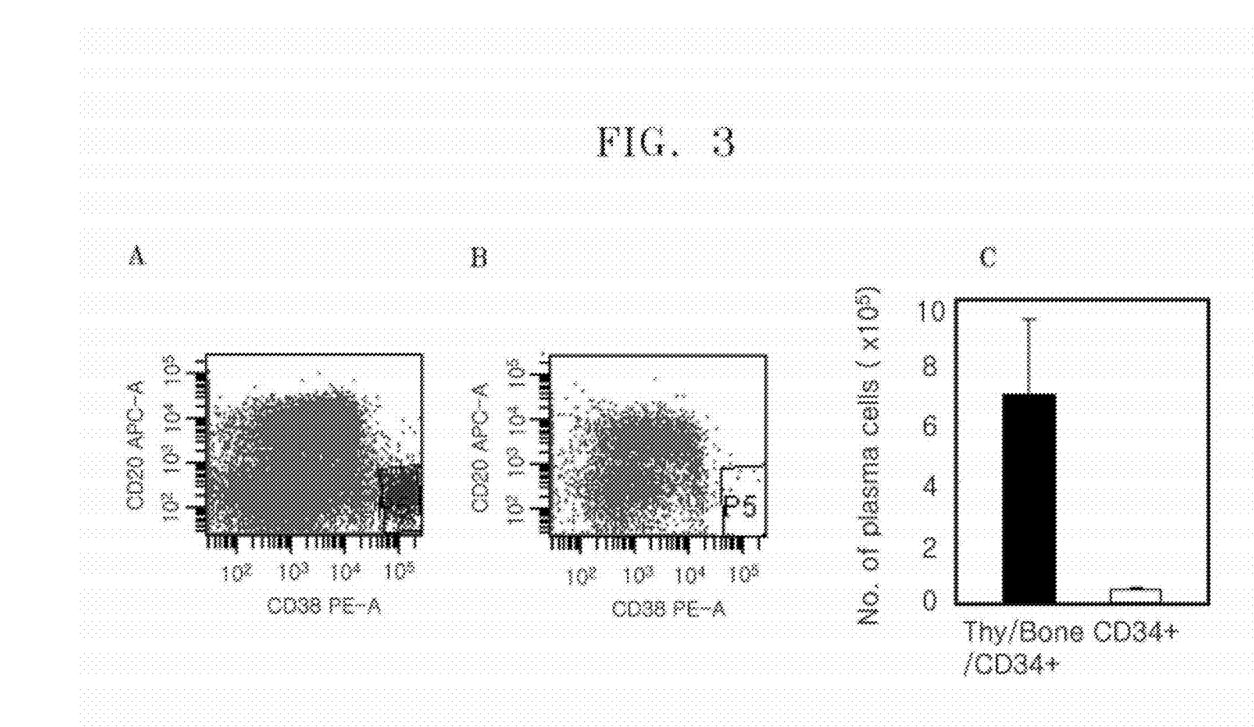
FIG. 3 is a view illustrating results obtained by staining the splenocytes with anti-human CD45-PECy7, anti-human CD20-APC, and anti-human CD38-PE.
Figure 4:
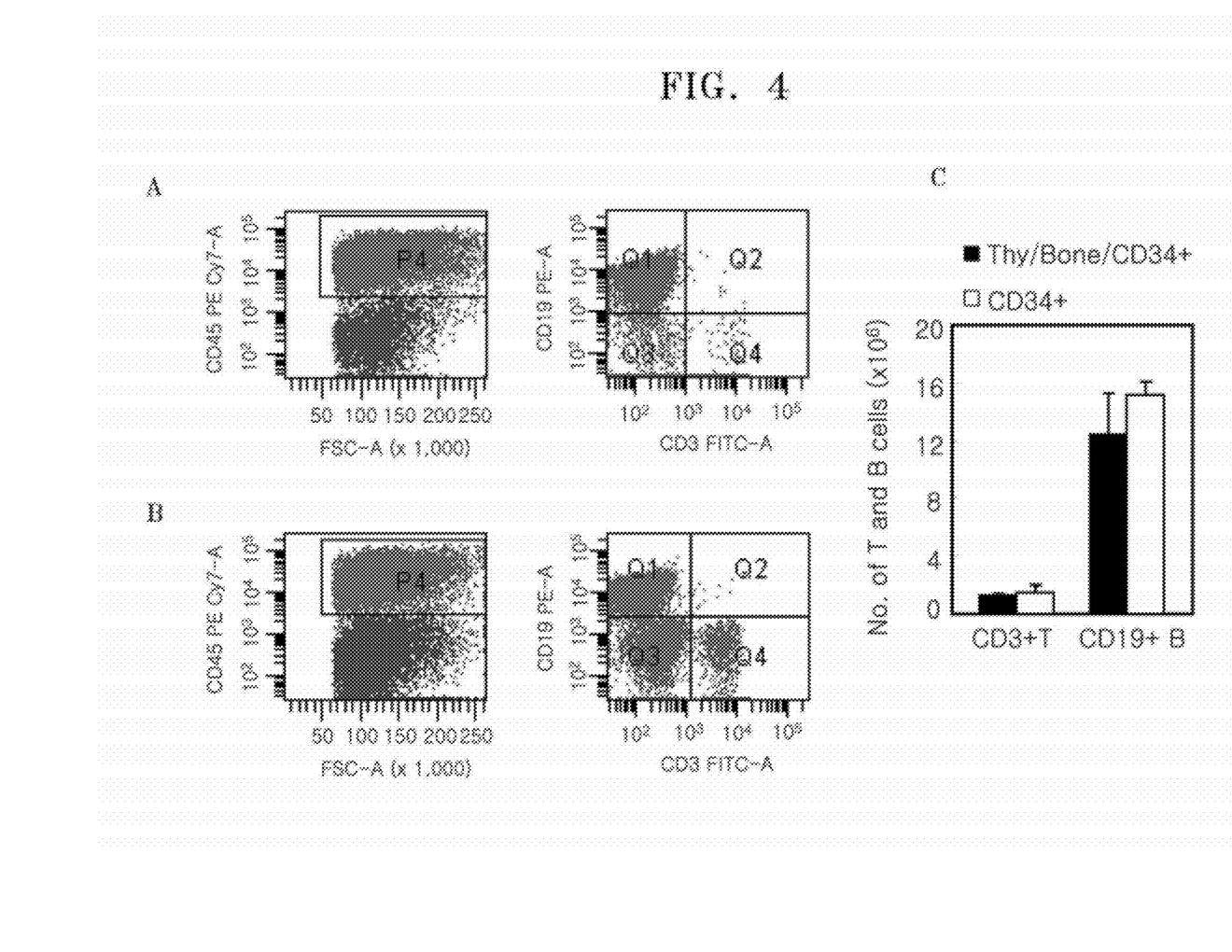
FIG. 4 is a view illustrating results obtained by staining myelocytes of the mice with anti-human CD45-PECy7, anti-human CD19-PE, and anti-human CD3-FITC.

FIG. 1 is a view illustrating splenocytes observed by FACS at 3 to 4 weeks after the final intrasplenic immunization of the mice with DNP-KLH. FIG. 1 shows results of the splenocytes with anti-human CD45-PECy7, anti-human CD19-PE, and anti-human CD3-FITC. FIG. 2 shows results of staining of the splenocytes of with anti-human CD19-PECy7, anti-human IgM-PE, and anti-human IgD-FITC. FIG. 3 shows results of staining with anti-human CD45-PECy7, anti-human CD20-APC, and anti-human CD38-PE, and FIG. 4 shows results observed after staining of bone marrow cells in the mice with anti-human CD45-PECy7, anti-human CD19-PE, and anti-human CD3-FITC.

In FIG. 1, A and B are the representative FACS profiles analyzed in human CD45+ cells for experimental (Thy/Bone/CD34+) and control group (CD34+), respectively, and C and D are bar graphs illustrating the analyzed results for experimental and control group, respectively. Mice which human fetal thymus, human fetal bone fragments, and human hematopoietic stem cells had been transplanted, contained more CD45+ cells (93.9%) which are human cells in spleen than those in a control group (68.5%). Human T and B cells, which were present in 42.5% and 45.5% based on the total CD45+ cells, respectively, were also present in spleen with higher number than those in a control group, which were present in 35.8% and 55.3% based on the total CD45+ cells, respectively.

FIG. 2 shows the representative FACS profiles of the mouse splenocytes of maturation of immature human B cells to T1 B cells (CD19+IgM+IgD−) and T2 B cells (CD19+IgM+IgD+) at developmental stages, and mature B cells (CD19+IgM-IgD+) (Immunological Reviews 2004. 197: 179-191) (A: experimental group (Thy/Bone/CD34+), B: control group (CD34+), C: bar representation of A and B). B cells, that is, CD19+ cells were found to be present in 46.9% based on the total cells for the experimental group and 29.1% based on the total cells for the control group. T1, T2, and mature B cells, which are present in 9.6%. 29.6% and 36.5% based on the total CD19+ cells, respectively were found to be present in spleens of mice which human fetal thymus and human fetal bone fragments had been transplanted with human hematopoietic stem cells with higher frequency than those in spleens of control mice, which are present in 7.8%. 20.4% and 47.6% based on the total CD19+ cells, respectively.

FIG. 3 shows the representative FACS profiles of CD38+++ CD20− cells (plasma cells) among CD45+ cells in the splenocytes of the mice. Plasma cells were present in the experimental group, which were present in 3.8% based on total CD45+ cells with higher ratios than those in the control group which only human hematopoietic stem cells had been transplanted, which were present in 0.2% based on total CD45+ cells (A: experimental group, B: control group, C: bar representation of A and B).

FIG. 4 is the representative FACS profiles of bone marrow cells at 3 to 4 weeks after intrasplenic immunization of NSG mice, which human fetal thymus, human fetal bone fragments, and human fetal liver-CD34+ cells had been transplanted, with DNP-KLH, that is, at 21 weeks after fetal liver-CD34+ hematopoietic stem cells had been transplanted (A: experimental group, B: control group, C: bar representation of A and B). FIG. 4 shows each result of staining with anti-human CD45-PECy7, anti-human CD19-PE, and anti-human CD3-FITC. FIG. 4 shows differentiation levels of T and B cells which are immune cells by engraftment of human hematopoietic stem cells in the mouse bone marrow. As shown in FIG. 4, CD45+ cells were present in 79.7% for the experimental group and 56.6% for the control group and CD3-CD19+ B cells and CD3+CD19− B cells were present in 57.3% and 5.8%, respectively for the experimental group and 60.4% and 7.7%, respectively for the control group.

It seems that human fetal thymus transplanted under the renal capsule provide an environment under which T cells may be developed and differentiated from hematopoietic stem cells and that fetal bone fragments subcutaneously transplanted provide a formation process of normal adult blood cells, in particular, a microenvironment under which B cells may be normally developed and differentiated, and induce differentiation into human mature B cells in NSG mice. As a result, as illustrated in FIG. 1 through 4, it is thought that development and differentiation into mature B cells has been enhanced. However, the scope of the present invention should not be limited to a certain mechanism.

When only CD34+ hematopoietic stem cells are transplanted into NSG mice, there are limitations in inducing development into T cells and development and differentiation into mature B cells with only thymus and bone tissues of NSG mice itself in long bone endosteal regions. However, because differentiation of human T cells may be induced by human fetal thymus tissues and differentiation and development of human fetal liver or umbilical cord blood-derived CD34+ hematopoietic stem cells into mature B cells which are closely related to human cells may be induced by human fetal bone fragments transplanted according to examples of the present invention, a humanized mouse model with a mature immune system may be obtained.

(4) Identification of Production of Antigen-Specific Monoclonal Antibodies in a Humanized Mouse Model in which Human Mature B Cells are Differentiated (4.1) Immunization with Antigen Antigen-immunization of a mouse model produced by transplantation of human fetal thymus, human fetal bone fragment, and human hematopoietic stem cells into NSG mice in an experimental group and a control group constructed as above is performed in the following manner. A first immunization was performed by administering DNP-KLH (Keyhole Limpet Hemocyanin, 100 μg/0.1 ml/mouse: Chemicon, USA) mixed with an incomplete adjuvant intramuscularly to mice at 14 weeks, post-transplantation of CD34+ human hematopoietic stem cells at 3 weeks, post-transplantation of human fetal thymus and fetal bone fragments. The second immunization was performed by injecting DNP-KLH (100 μg/0.1 ml/mouse: Chemicon, USA) mixed with a complete adjuvant intramuscularly into mice at 2 weeks after the first immunization. At 2 weeks after the second immunization, the mice were anesthetized, followed by intrasplenic injection of DNP-KLH (100 µg/0.1 ml/mouse: Chemicon, USA) into the mice. At 3 to 4 weeks after the intrasplenic injection, spleen of the mouse were harvested and ¼ of the spleen was fixed with formalin for immunohistochemical staining.

Figure 5:
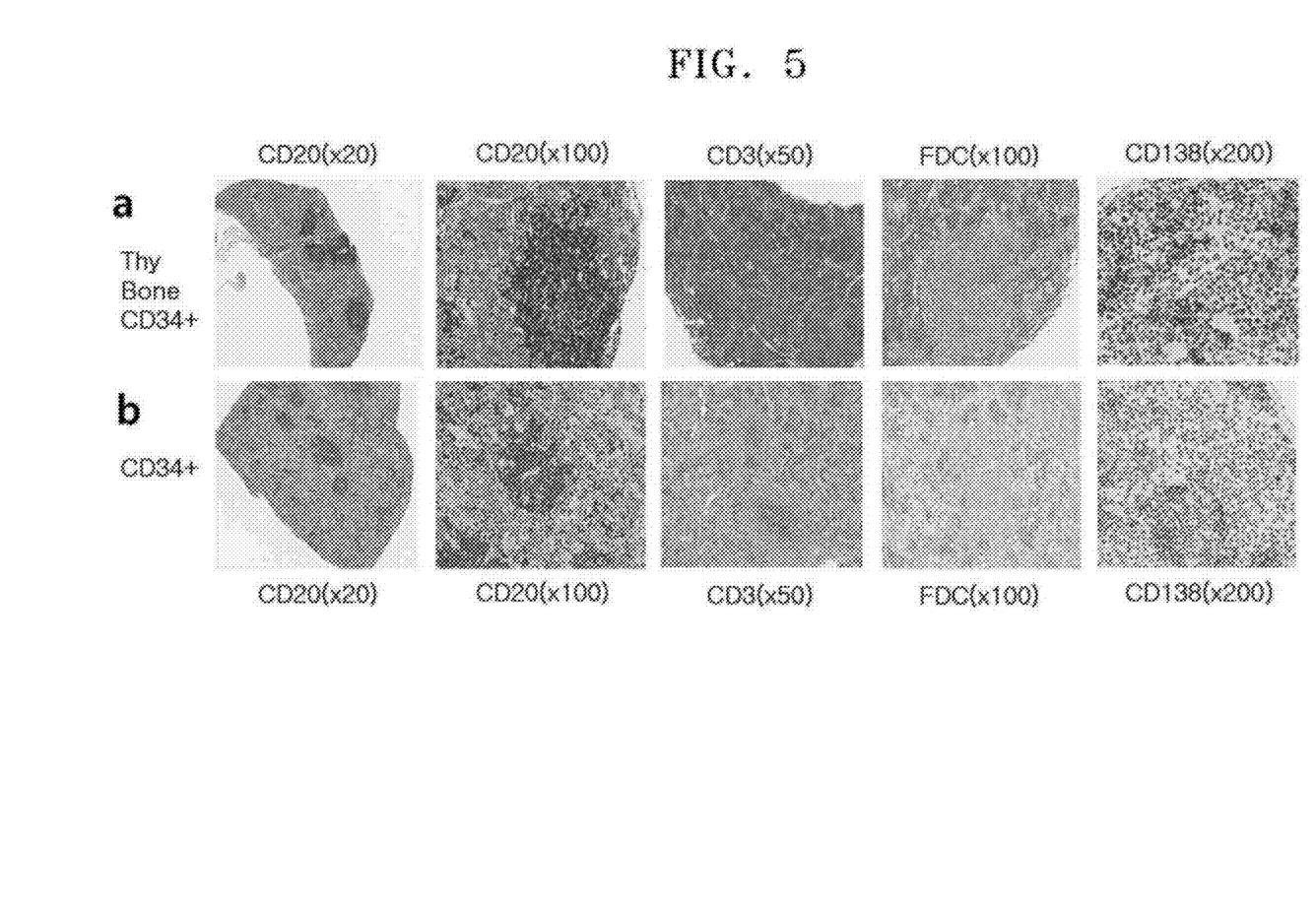
FIG. 5 is a group of photos illustrating results of immunohistochemical staining of the DNP-KLH immunized spleens of NSG mice which human fetal thymus, fetal bone fragment, and hematopoietic stem cells are transplanted (a) and a group of photos illustrating results of immunohistochemical staining of the DNP-KLH immunized spleens of NSG mice which only hematopoietic stem cells are transplanted (b)

FIG. 5a (experimental group) and FIG. 5b (control group) are views illustrating results of immunohistochemical staining of the spleens obtained at 3 weeks after final immunization of NSG mice, which human fetal thymus, fetal bone fragment, and hematopoietic stem cells had been transplanted, with DNP-KLH. As illustrated in FIGS. 5a and 5b, CD3+ T cell zone and CD20+ B cell zone were well distinguished and developed in spleens which human fetal thymus/human fetal bone fragments/human hematopoietic stem cells had been transplanted. The high frequencies of human follicular dendritic cells (FDC+) and human CD138+ plasma cells were developed in the mouse spleen. Conversely, there were not obvious in the boundaries between CD3+ T cell zone and CD20+ B cell zone of the spleens which only human hematopoietic stem cells had been transplanted, and in particular, CD138+ plasma cells were very poorly differentiated.

Figure 6:
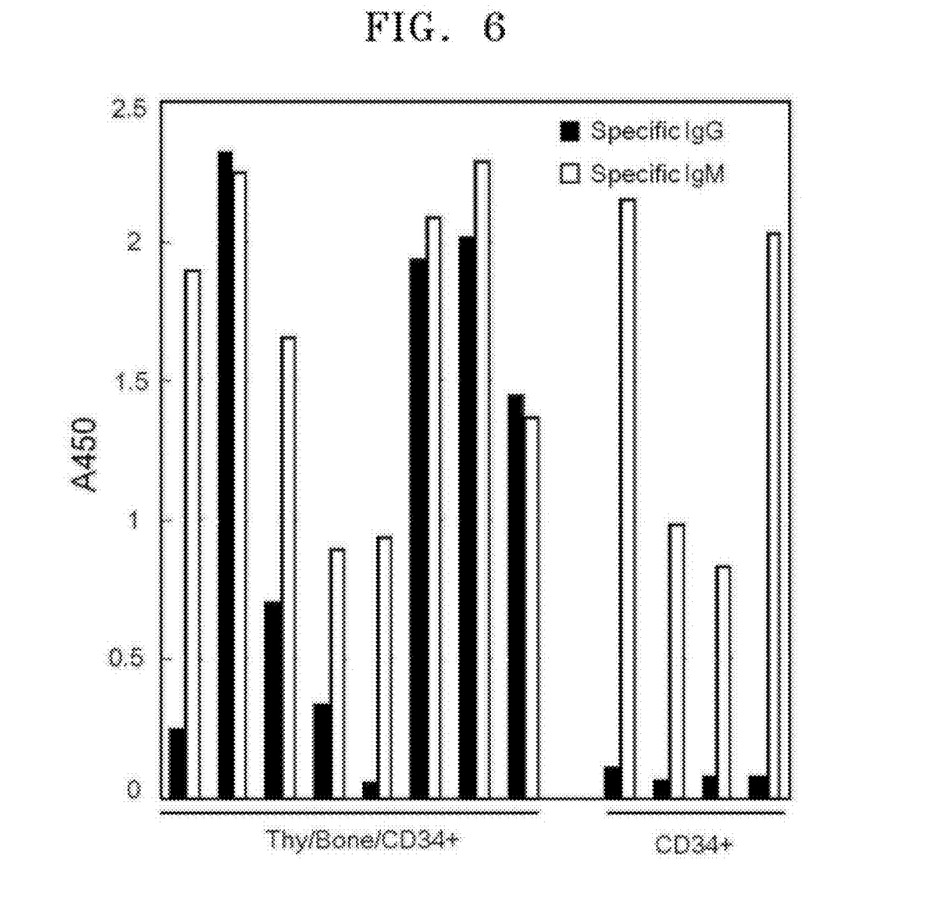
FIG. 6 is a graph illustrating results of ELISA analysis of DNP-KLH specific human IgG and IgM present in sera of the immunized NSG mice which human fetal thymus, human fetal bone fragment, and/or hematopoietic stem cells are transplanted.

Blood was collected from the caudal veins of the DNP-KLH immunized NSG mice which human fetal thymus, fetal bone fragment, and/or hematopoietic stem cells had been transplanted, and antigen-specific IgG and IgM in sera were examined. FIG. 6 is a graph illustrating results of ELISA analysis of antigen-specific human IgG and IgM present in sera of the DNP-KLH immunized NSG mice which human fetal thymus, human fetal bone fragment, and/or human hematopoietic stem cells had been transplanted. As illustrated in FIG. 6, DNP-KLH-specific IgG (black bar) and IgM (white bar) were detected in sera of the mice which human hematopoietic stem cells had been transplanted along with human fetal thymus and human fetal bone fragment. However, DNP-KLH-specific IgM was present, but antigen-specific IgG was rarely detected, in sera of the mice in which only human hematopoietic stem cells had been transplanted.

(4.2) Immortalization of Cells Producing Antigen-Specific Antibodies

Splenocytes were prepared from some of the remaining (¾) spleens which had been harvested in (4.1). The splenocytes prepared were subjected to cell fusion with a myeloma cell line (mouse-human chimeric cell) to select the immortalized cells producing DNP-specific monoclonal human antibodies. As a result, $1.7 \times 10^7$ cells were fused with myeloma cells to select 180 immortalized cell clones. It was confirmed that human antibodies were detected in about 70 clones among them, most of the clones produced human specific IgM, and 2 clones produced human specific IgG (OD: 0.3 to 1.5). Among them, one cell producing DNP-KLH specific human IgM was referred to as clone No. 3, while one cell producing DNP-KLH specific human IgG was referred to as clone No. 56. The obtained clones, named No. 3 and 56, were incubated in RPMI 1640 media with 10% FBS medium in a 96-well plate (37° C., 5% $CO_2$). Supernatants obtained from the cultures were subjected to ELISA. The ELISA procedure was performed in the following procedure. First, each well of a 96-well plate was coated with DNP-KLH. After wash, blocking was performed, followed by wash. Next, the supernatant samples were added and reacted with labeled anti-human IgM (Bethyl Laboratory, USA) and anti-human IgG (Bethyl Laboratory, USA) antibodies, followed by wash. TMB and stop solution was added and the absorbancy was measured at 450 nm (A450). Table 1 shows the results of measurement at 450 nm (A450), with an average of two repeated experimental values.

Table 1

TABLE 1

| Medium | Supernatant of clone No. 56 (IgG) | Supernatant of clone No. 3 (IgM) |
| --- | --- | --- |
| 0.059 | 0.289 | 1.4285 |

As a control group, experiments were performed in the same manner, except that BSA was used instead of DNP-KLH, and the results are shown in Table 2.

Table 2

TABLE 2

| Medium | Supernatant of clone No. 56 (IgG) | Supernatant of clone No. 3 (IgM) |
| --- | --- | --- |
| 0.046 | 0.047 | 0.059 |

As illustrated in Table 1, each of IgG and IgM may be produced with high productivity from the hybridoma clones No. 56 and 3.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An NSG mouse into which isolated human fetal thymus, isolated human fetal bone fragment, and isolated human hematopoietic stem cells are transplanted, wherein the NSG mouse is not transplanted with isolated human fetal liver tissues;
   said NSG mouse exhibiting development and in vivo differentiation of human T cells and B cells from human hematopoietic stem cells and a level of antigen specific human IgG monoclonal antibody that is higher than in NSG mice in which only human hematopoietic stem cells are transplanted.

2. The NSG mouse of claim 1, wherein the human fetal thymus is transplanted under a renal capsule, the human fetal bone fragment is transplanted subcutaneously, and the human hematopoietic stem cells are intravenously transplanted.

3. The NSG mouse of claim 1, wherein the human hematopoietic stem cells are human fetal liver or umbilical cord blood-derived CD34+ cells.

4. A method of producing a humanized mouse that exhibits development and in vivo differentiation of human T cells and B cells from human hematopoietic stem cells and a level of antigen specific human IgG monoclonal antibody that is higher than in NSG mice in which only human hematopoietic stem cells are transplanted, comprising: transplanting isolated human fetal thymus, isolated human fetal bone fragment, and isolated human hematopoietic stem cells into an NSG mouse, wherein the NSG mouse is not transplanted with isolated human fetal liver tissues.

5. The method of claim 4, wherein the human fetal thymus is transplanted under a renal capsule, the human fetal bone fragment is transplanted subcutaneously, and the human hematopoietic stem cells are intravenously transplanted.

* * * * *

UNITED STATES PATENT AND TRADEMARK OFFICE
CERTIFICATE OF CORRECTION

PATENT NO. : 8,604,271 B2
APPLICATION NO. : 13/227233
DATED : December 10, 2013
INVENTOR(S) : Sung Joo Kim et al.

It is certified that error appears in the above-identified patent and that said Letters Patent is hereby corrected as shown below:

Title Page, Items (75) Inventors: fourth inventor should read -- Bong Kum Choi, Masan-si (KR) --

(73) Assignee: should read -- Samsung Life Public Welfare Foundation (KR) --

Signed and Sealed this
Fifteenth Day of April, 2014

Michelle K. Lee
*Deputy Director of the United States Patent and Trademark Office*